US012778800B2

(12) United States Patent
Grüebler et al.

(10) Patent No.: US 12,778,800 B2
(45) Date of Patent: Nov. 3, 2026

(54) APPARATUS FOR SUBRETINAL INJECTION

(71) Applicant: Alcon Inc., Fribourg (CH)

(72) Inventors: Reto Grüebler, Greifensee (CH); Thomas Linsi, Schaffhausen (CH)

(73) Assignee: Alcon Inc., Fribourg (CH)

( * ) Notice: Subject to any disclaimer, the term of this patent is extended or adjusted under 35 U.S.C. 154(b) by 810 days.

(21) Appl. No.: 17/935,661

(22) Filed: Sep. 27, 2022

(65) Prior Publication Data

US 2023/0111131 A1 Apr. 13, 2023

Related U.S. Application Data

(60) Provisional application No. 63/250,383, filed on Sep. 30, 2021.

(51) Int. Cl.

| | |
|---|---|
| ***A61M 5/14*** | (2006.01) |
| ***A61F 9/007*** | (2006.01) |
| *A61M 5/145* | (2006.01) |
| *A61M 5/168* | (2006.01) |
| *A61M 5/178* | (2006.01) |
| *A61M 5/19* | (2006.01) |

(52) U.S. Cl.

CPC .......... *A61F 9/007* (2013.01); *A61F 9/00736* (2013.01); *A61M 5/1408* (2013.01); *A61M 2005/14513* (2013.01); *A61M 5/16827* (2013.01); *A61M 2005/1787* (2013.01); *A61M 5/19* (2013.01)

(58) Field of Classification Search

CPC .. A61M 5/19; A61M 5/1408; A61M 5/31596; A61M 3/005; A61M 39/225; A61M 2039/224; A61M 2005/1787; A61M 5/16827; A61M 2005/14513; A61F 9/00736

USPC .......................................................... 604/181

See application file for complete search history.

(56) References Cited

U.S. PATENT DOCUMENTS

| | | | | |
|---|---|---|---|---|
| 5,830,214 | A * | 11/1998 | Flom | A61B 18/1482 604/35 |
| 7,601,140 | B2 | 10/2009 | Rossback | |
| 8,177,747 | B2 | 5/2012 | Pinedjian | |
| 9,517,162 | B2 | 12/2016 | Huculak | |

(Continued)

FOREIGN PATENT DOCUMENTS

| | | | |
|---|---|---|---|
| CN | 205994817 | U | 3/2017 |
| JP | 2014050552 | A | 3/2014 |
| JP | 2017500123 | A | 1/2017 |

*Primary Examiner* — Emily L Schmidt
*Assistant Examiner* — Martin A Radomski
(74) *Attorney, Agent, or Firm* — Patterson + Sheridan, LLP

(57) ABSTRACT

An apparatus disclosed herein may include a housing, an injection line sub-assembly coupled to a distal end of the housing, a fluid selector coupled to the housing and movable between a first position and a second position, a drug container coupled to the housing and disposed between the fluid selector and the sub-assembly, and a drug container bypass line coupled to the housing and disposed between the fluid selector and the sub-assembly. When the fluid selector is in the first position, a first outlet of the fluid selector is in fluid communication with the drug container bypass line for injecting a fluid through the drug container bypass line and into the sub-assembly. When the fluid selector is in the second position, a second outlet of the fluid selector is in fluid communication with the drug container for injecting a drug from the drug container into the sub-assembly.

10 Claims, 10 Drawing Sheets

(56) References Cited

U.S. PATENT DOCUMENTS

| | | | | |
|---|---|---|---|---|
| 9,987,163 | B2 | 6/2018 | Schaller | |
| 10,010,447 | B2 | 7/2018 | Kashani | |
| 10,434,010 | B2 | 10/2019 | Auld | |
| 2006/0167415 | A1* | 7/2006 | Nemoto | A61M 5/1456 604/154 |
| 2007/0038174 | A1 | 2/2007 | Hopkins | |
| 2007/0060887 | A1 | 3/2007 | Marsh | |
| 2010/0286650 | A1* | 11/2010 | Fitzgerald | A61J 1/1412 604/249 |
| 2015/0164687 | A1* | 6/2015 | Kashani | A61M 5/178 604/154 |
| 2015/0190589 | A1 | 7/2015 | Bryant et al. | |
| 2015/0250952 | A1 | 9/2015 | Naftalovitz et al. | |
| 2016/0074217 | A1* | 3/2016 | Khan | A61F 9/0017 604/156 |
| 2017/0360606 | A1* | 12/2017 | Price | A61B 46/23 |
| 2017/0360607 | A1 | 12/2017 | Price | |
| 2018/0132990 | A1* | 5/2018 | Baeten | A61C 1/02 |
| 2019/0105197 | A1 | 4/2019 | Labelle | |
| 2021/0169689 | A1 | 6/2021 | Bley et al. | |
| 2022/0233768 | A1 | 7/2022 | Abt et al. | |

* cited by examiner

APPARATUS FOR SUBRETINAL INJECTION

PRIORITY CLAIM

This application claims the benefit of priority of U.S. Provisional Patent Application Ser. No. 63/250,383 titled "APPARATUS FOR SUBRETINAL INJECTION," filed on Sep. 30, 2021, whose inventors are Reto Grüebler and Thomas Linsi, which is hereby incorporated by reference in its entirety as though fully and completely set forth herein.

BACKGROUND

Certain diseases of the eye are treatable via injection into the subretinal space including, e.g., age-related macular degeneration (AMD), diabetic macular edema, proliferative diabetic retinopathy, other retinal degenerative diseases, and genetic defects. The term "subretinal space" refers to a location between the retina and retinal pigment epithelium (RPE) of the eye. Injection of fluids and/or drugs into the subretinal space may be referred to as "subretinal injection." As used herein, the term "drug" may refer to drugs, therapeutics, stem cells, or gene vectors.

Common practice requires at least two persons to administer a subretinal injection. For example, a lead surgeon may guide the injection instrument, e.g., a syringe/needle, and visually monitor the injection site, while a skilled surgical assistant dispenses the fluid from the syringe and monitors the injection volume. In some examples (described below), two separate injection steps are performed with different needles. Alternatively, premixing may be used to avoid performing two separate injection steps. For example, in the first step of the procedure, a first needle coupled to a syringe containing a fluid, e.g., balanced salt solution (BSS), is inserted through the retina and into the subretinal space. In this example, while the surgeon handles the syringe and visually monitors the injection site, the assistant manually injects the fluid and monitors the injection volume. Then, the first needle is removed from the eye. The fluid is used to open up the subretinal space in preparation for injection of a drug as described below.

In the second step of the procedure, a second needle coupled to a syringe containing a drug is inserted through the retina and into the subretinal space at about the same location as the first needle. In this example, while the surgeon handles the syringe and visually monitors the injection site, the assistant manually injects the drug and monitors the injection volume.

Removing the first needle and inserting the second needle through the retina, as described above, can have several disadvantages. For example, making multiple insertions through the retina increases the potential for retinal tearing. In addition, the first and second needles are likely to puncture the retina in different locations, which increases the potential for fluid to leak from the subretinal space.

Each of the problems described above can negatively affect the ophthalmic treatment being administered and/or carry an increased safety risk. Therefore, what is needed in the art are improved devices for ophthalmic treatment including an improved apparatus and method for subretinal injection.

SUMMARY

The present disclosure generally relates to devices for ophthalmic treatment, and more particularly, to an apparatus and method for performing subretinal injection.

An apparatus disclosed herein may include a housing, an injection line sub-assembly coupled to a distal end of the housing, a fluid selector coupled to the housing and movable between a first position and a second position, a drug container coupled to the housing and disposed between the fluid selector and the sub-assembly, and a drug container bypass line coupled to the housing and disposed between the fluid selector and the sub-assembly. The drug container bypass line may be connected in parallel with the drug container. When the fluid selector is in the first position, a first outlet of the fluid selector is in fluid communication with the drug container bypass line for injecting a fluid through the drug container bypass line and into the sub-assembly. When the fluid selector is in the second position, a second outlet of the fluid selector is in fluid communication with the drug container for injecting a drug from the drug container into the sub-assembly.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 1B illustrates the injection apparatus in a protracted state.

FIG. 1D illustrates the injection apparatus in a first state for injecting a fluid.

FIG. 6A illustrates the injection apparatus in a retracted state.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to devices for ophthalmic treatment, and more particularly, to an apparatus and method for performing subretinal injection.

Embodiments of the present disclosure describe an apparatus for performing a subretinal injection. In general, the apparatus includes a housing, which facilitates surgical manipulation. A slidable injection line sub-assembly is coupled to a distal end of the housing for protracting and retracting a needle relative to an outer tube. Note that, as described herein, a distal end or portion of a component refers to the end or the portion that is closer to a patient's body during use thereof. On the other hand, a proximal end or portion of the component refers to the end or the portion that is distanced further away from the patient's body. The needle may be retracted inside the outer tube as the outer tube is inserted into the eye, e.g., through a valved cannula (shown in FIG. 5A). Retraction of the needle inside the outer tube avoids contact between the needle and the valved cannula and enables the outer tube to be more easily and safely inserted into the eye. After the outer tube is inserted into the eye, the needle may be protracted to extend the needle at least partially outside the outer tube (shown in FIG. 5B) to enable the needle to be inserted into the subretinal space (shown in FIG. 5C).

The apparatus may include a drug container and a drug container bypass line, which are connected in parallel to enable both a drug and a fluid to be stored inside and/or injected using the same apparatus. A fluid selector may be coupled to the housing and movable between a first position and a second position in order to switch between injection of the fluid and the drug, respectively. When the fluid selector is in the first position, a first outlet of the fluid selector is in fluid communication with the drug container bypass line for injecting the fluid through the drug container bypass line and into the sub-assembly leading to the eye. When the fluid selector is in the second position, a second outlet of the fluid selector is in fluid communication with the drug container for injecting the drug from the drug container into the sub-assembly leading to the eye. Thus, the fluid selector enables both the fluid and the drug to be administered from the same needle, in contrast to typical practice, described above, which uses two separate injection steps with different needles.

Figure 1A:
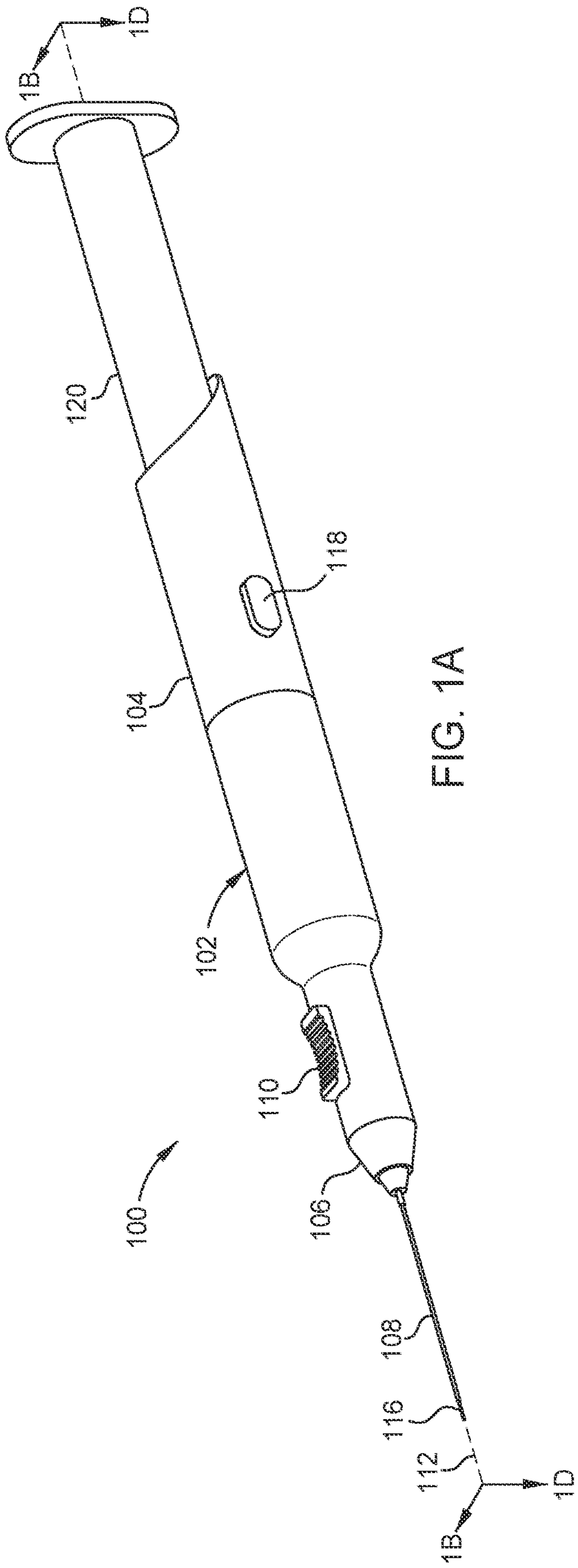
FIG. 1A is an isometric view of an exemplary injection apparatus for performing a subretinal injection, according to certain embodiments.

FIG. 1A is an isometric view of an exemplary injection apparatus 100 for performing a subretinal injection, according to certain embodiments. Injection apparatus 100 generally includes a housing 102 (also referred to as a "handpiece"). As shown, housing 102 generally includes a housing body 104 and a cap 106. Cap 106 is coupled to a distal end of housing body 104. An outer tube 108 is coupled to a distal end of housing 102. In the illustrated embodiments, outer tube 108 is coupled to cap 106 (shown in FIG. 1B).

An actuator 110 is disposed through a wall of housing body 104. An outer part of actuator 110, which is shown in FIG. 1A, is configured such that it can be pushed and pulled, e.g., by a user's finger. Actuator 110 is slidable relative to housing 102 in a direction parallel to a longitudinal axis 112 of housing 102. Actuator 110 is coupled to an injection line sub-assembly (shown as sub-assembly 114 in FIG. 1B). While the sub-assembly includes multiple components, only needle 116 thereof extends outside outer tube 108 and is therefore visible in FIG. 1A. The sub-assembly is slidably disposed through outer tube 108. Thus, actuator 110 is slidable to retract and protract the sub-assembly including needle 116 in relation to outer tube 108. As shown in FIG. 1A, needle 116 is fully protracted. In this position, needle 116 is disposed at least partially outside a distal end of outer tube 108.

A fluid selector 118 is disposed through the wall of housing body 104. Fluid selector 118 is movable relative to housing 102 in a direction perpendicular to longitudinal axis 112 of housing 102. Fluid selector 118 is configured to control routing of flow through multiple different pathways within injection apparatus 100 as described in detail below. An outer part of fluid selector 118, which is shown in FIG. 1A, is configured such that it can be pushed, e.g., by a user's finger. Although not shown in FIG. 1A, an opposite end of fluid selector 118 is also configured such that it can be pushed, e.g., by a user's finger, in the opposite direction. A syringe 120 is coupled to a proximal end of injection apparatus 100. While syringe 120 generally includes a syringe barrel and a plunger, for clarity, only the syringe barrel is shown in the illustrated embodiments. Syringe 120 may contain a fluid, which can be used to drive flow through injection apparatus 100.

Figures 1B, 1C, 1D:
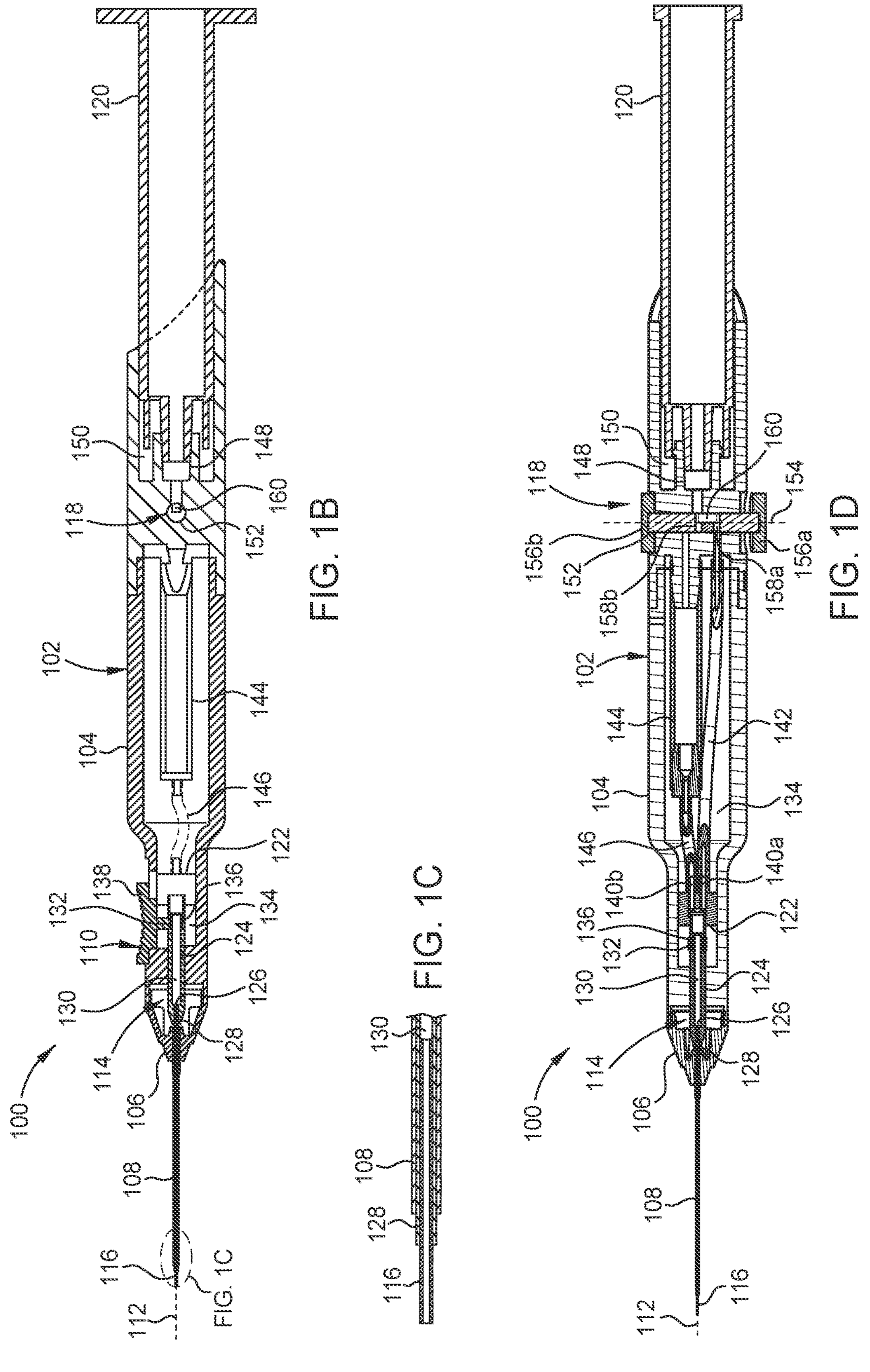
FIG. 1B is a cross-sectional view of the injection apparatus of FIG. 1A taken along section line 1B-1B, which illustrates the injection apparatus when viewed from the right side, according to certain embodiments.
FIG. 1C is an enlarged cross-sectional view of a portion of FIG. 1A, according to certain embodiments.
FIG. 1D is a cross-sectional view of the injection apparatus of FIG. 1A taken along section line 1D-1D, which illustrates the injection apparatus when viewed from top-down, according to certain embodiments.

FIG. 1B is a cross-sectional view of injection apparatus 100 of FIG. 1A taken along section line 1B-1B, which illustrates injection apparatus 100 when viewed from the right side, according to certain embodiments. FIG. 1B illustrates injection apparatus 100 in a protracted state. In the protracted state, needle 116 is disposed at least partially outside a distal end of outer tube 108, as described above. Sub-assembly 114 includes a first piece 122 and a second piece 124 disposed in the distal end of housing 102. In the illustrated embodiments, first piece 122 and second piece 124 are coupled together. Note that, as described herein, the term "coupled" may refer to separate pieces, which are connected together or to different parts of a single piece. In certain embodiments, first piece 122 and second piece 124 are a single piece. Therefore, first piece 122 and second piece 124 may be referred to collectively as a "body" of sub-assembly 114. As shown, first piece 122 contacts the wall of housing body 104. In the illustrated embodiments, second piece 124 is disposed through a center aperture of first piece 122 such that first piece 122 centralizes second piece 124 in relation to the wall of housing body 104. Second piece 124 has a single outlet 126 at its distal end. An inner tube 128 is coupled to the distal end of second piece 124. Inner tube 128 is in fluid communication with outlet 126 of second piece 124. As shown in more detail in FIG. 1C, inner tube 128 is at least partially disposed in outer tube 108. Needle 116 is coupled to a distal end of inner tube 128 (shown in FIG. 1C). Thus, a continuous flow path 130 is formed through each piece of sub-assembly 114 between an inlet of first piece 122 and an outlet of needle 116.

Figure 2:
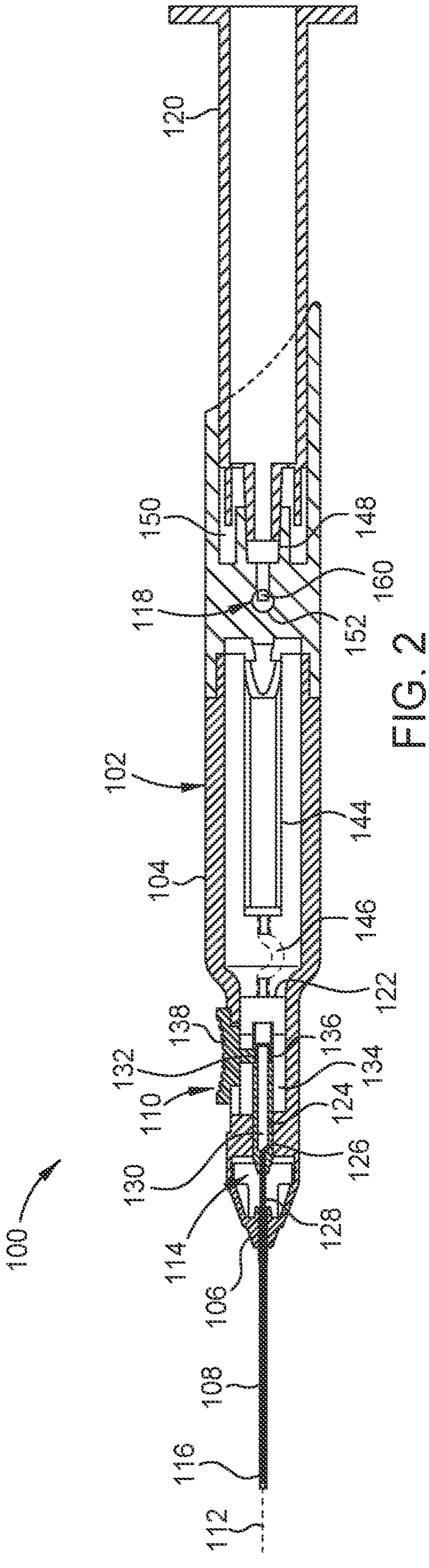
FIG. 2 illustrates the injection apparatus of FIG. 1A in a retracted state, according to certain embodiments.

Actuator 110 has a catch 132 which extends inside a cavity 134 of housing body 104. Catch 132 engages second piece 124 of sub-assembly 114 in order to couple actuator 110 to sub-assembly 114. In the illustrated embodiments, catch 132 fits into a corresponding profile 136 formed in an outer surface of second piece 124, although other attachment types are contemplated. An outer part 138 of actuator 110 is configured such that it can be pushed and pulled, e.g., by a user's finger, as described above. Actuator 110 is able to slide in a direction parallel to longitudinal axis 112 to switch between a fully protracted position (shown in FIG. 1B) and a fully retracted position (shown in FIG. 2). When actuator 110 is pushed or pulled in a distal direction in relation to housing 102, sub-assembly 114 is moved to the fully protracted position (shown in FIG. 1B). In the fully protracted position, a distal end of actuator 110 contacts housing body 104 to prevent further movement of actuator 110 in the distal direction in relation to housing 102. Likewise, when actuator 110 is pushed or pulled in a proximal direction in relation housing 102, sub-assembly 114 is moved to the fully retracted position (shown in FIG. 2). In the fully retracted position, needle 116 is disposed entirely inside outer tube 108. In the fully retracted position, a proximal end of actuator 110 contacts housing body 104 to prevent further movement of actuator 110 in the proximal direction in relation to housing 102.

FIG. 1D is a cross-sectional view of injection apparatus 100 of FIG. 1A taken along section line 1D-1D which illustrates injection apparatus 100 when viewed from top-down, according to certain embodiments. FIG. 1D illustrates injection apparatus 100 in a first state for injecting a fluid. As shown in FIG. 1D, sub-assembly 114 includes a pair of inlets 140 (140*a*-*b*) which are each in fluid communication with flow path 130. Injection apparatus 100 includes a drug container bypass line 142 coupled to housing 102. Drug container bypass line 142, which is housed inside cavity 134 of housing body 104, is disposed between fluid selector 118 and sub-assembly 114. A proximal end of drug container bypass line 142 is coupled to housing body 104. A distal end of drug container bypass line 142 is in fluid communication with a first inlet 140*a* of sub-assembly 114. The distal end of drug container bypass line 142 is directly coupled to first inlet 140*a*. In the illustrated embodiments, drug container bypass line 142 consists of a piece of flexible tubing. Thus, drug container bypass line 142 allows relative movement between sub-assembly 114 and housing 102 during retraction and protraction of sub-assembly 114.

Injection apparatus 100 includes a drug container 144 coupled to housing 102. Like drug container bypass line 142, drug container 144, which is housed inside cavity 134 of housing body 104, is disposed between fluid selector 118 and sub-assembly 114. Drug container 144 is connected in parallel with drug container bypass line 142. A proximal end of drug container 144 is coupled to housing body 104. A distal end of drug container 144 is in fluid communication with a second inlet 140*b* of sub-assembly 114 through a piece of flexible tubing 146, which is similar to the flexible tubing of drug container bypass line 142. Flexible tubing 146 is fluidly coupled between drug container 144 and second inlet 140*b*. Flexible tubing 146 allows relative movement between sub-assembly 114 and drug container 144 during retraction and protraction of sub-assembly 114.

Injection apparatus 100 includes a port 148 at the proximal end of housing body 104. As shown, syringe 120 is coupled to port 148 through a Luer-Lock style connection, although other connection types are contemplated. Syringe 120 is disposed at least partially in a cavity 150 of housing body 104. Cavity 150 is spaced from cavity 134 in a proximal direction in relation to housing 102. In some other embodiments, instead of directly coupling syringe 120 to injection apparatus 100, syringe 120 may be coupled indirectly to injection apparatus 100 (e.g., using a length of tubing disposed in between syringe 120 and port 148). For example, the tubing may be coupled to port 148 and extend beyond the proximal end of housing body 104 for coupling to syringe 120. Indirectly coupling syringe 120 to injection apparatus 100 enables a reduction in the length of injection apparatus 100 due to the removal of the connection features on port 148. In turn, the reduced length makes injection apparatus 100 more ergonomic and balanced.

Figure 3:
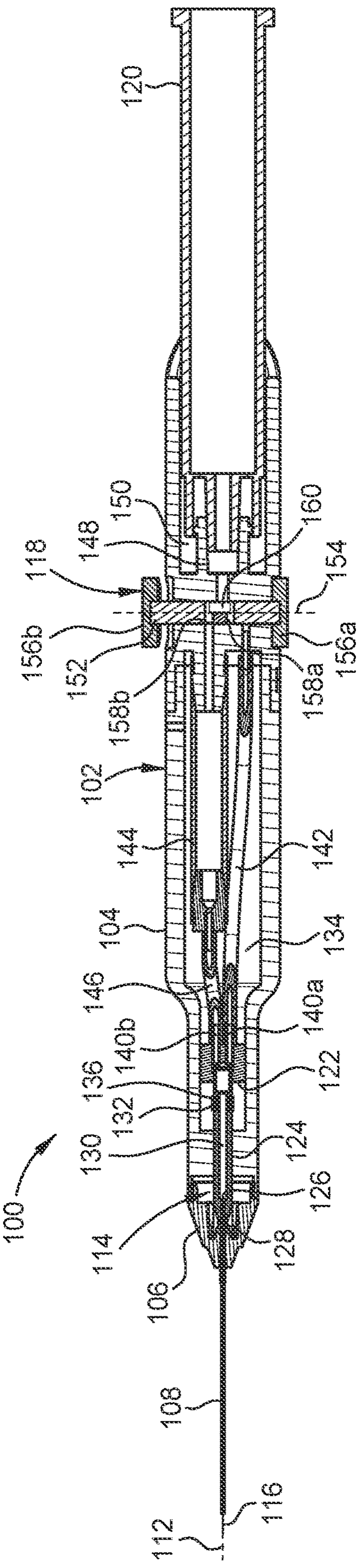
FIG. 3 illustrates the injection apparatus of FIG. 1A in a second state for injecting a drug, according to certain embodiments.

In the illustrated embodiments, fluid selector 118 is disposed between port 148 and each of drug container bypass line 142 and drug container 144. In some other embodiments, fluid selector 118 is disposed in a distal direction in relation to each of drug container bypass line 142 and drug container 144 (e.g., between actuator 110 and each of drug container bypass line 142 and drug container 144). Positioning fluid selector 118 closer to actuator 110 may improve the ergonomics of injection apparatus 100. In some other embodiments, fluid selection for injection apparatus 100 may be implemented using aspects shown in FIGS. 9 and 10. In the illustrated embodiments, fluid selector 118 generally includes a pin 152 disposed through a corresponding aperture formed in housing body 104. Pin 152 is disposed transverse to housing body 104. In other words, a longitudinal axis 154 of pin 152 is perpendicular to longitudinal axis 112 of housing 102. Thus, pin 152 is able to translate on longitudinal axis 154 through the corresponding aperture to switch fluid selector 118 between a first state (shown in FIG. 1D) and a second state (shown in FIG. 3). As shown, pin 152 includes caps 156 (156*a*-*b*) at opposite ends, which are larger in diameter compared to pin 152. Caps 156 retain pin 152 within housing body 104 while also facilitating manipulation of fluid selector 118, e.g., by a user's finger. Caps 156 may be omitted in some other embodiments.

Pin 152 includes a pair of outlets 158 (158*a*-*b*) and a single inlet 160 which are in fluid communication with each other. Outlets 158 and inlet 160 are disposed transverse to longitudinal axis 154 of pin 152. Outlets 158 are spaced from each other relative to longitudinal axis 154. Inlet 160 is in fluid communication with port 148 when fluid selector 118 is in either of the first state (shown in FIG. 1D) or the second state (shown in FIG. 3), as described in more detail below.

In the first state (shown in FIG. 1D), a first outlet 158*a* of fluid selector 118 is in fluid communication with drug container bypass line 142. In this position, a second outlet 158*b* of fluid selector 118 is closed off from fluid communication with drug container 144. In this position, a fluid, which may be contained in drug container bypass line 142 and/or syringe 120 is injected into the eye through first inlet 140*a* and through flow path 130 of sub-assembly 114. In certain embodiments, flow through injection apparatus 100 is driven by a fluid received from syringe 120 (shown in FIG. 1D). Alternatively, in some other embodiments, port 148 is coupled to an external pressure source for driving flow through injection apparatus 100. In some examples, the external pressure source may include a pressure control pump, e.g., a Vernier Flow Control (VFC) pump, a volume control pump, a variable volume control pump, a peristaltic pump, a lever-actuated pump, a valve-actuated pump, or a venturi pump.

In the second state (shown in FIG. 3), second outlet 158*b* of fluid selector 118 is in fluid communication with drug container 144. In this position, first outlet 158*a* of fluid selector 118 is closed off from fluid communication with drug container bypass line 142. In this position, the drug contained in drug container 144, is injected into the eye through second inlet 140*b* and through flow path 130 of sub-assembly 114. As described above, flow through injection apparatus 100 may be driven by a syringe or, alternatively, by an external pressure source.

Figure 4:
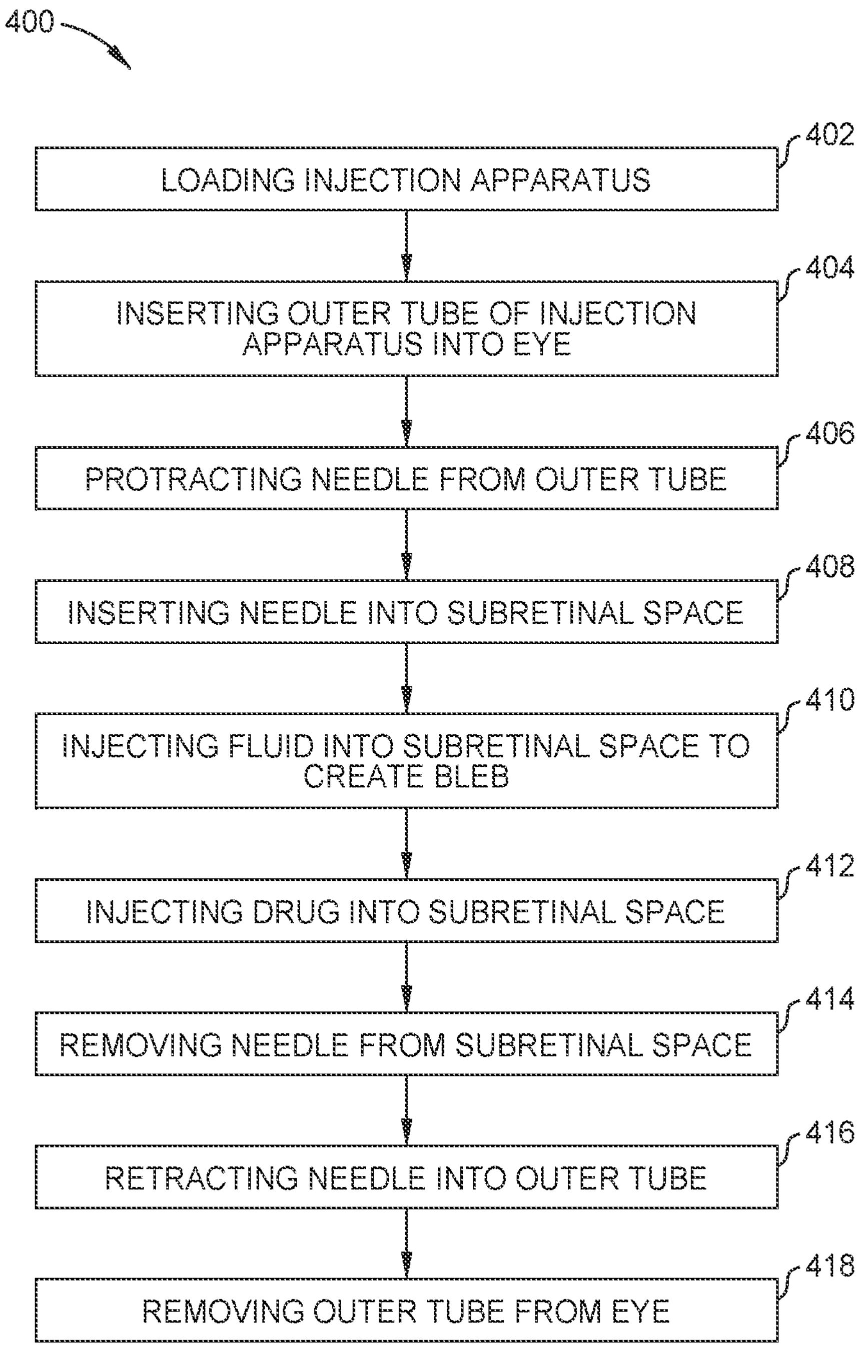
FIG. 4 illustrates a method for performing a subretinal injection using the injection apparatus of FIG. 1A, according to certain embodiments.

FIG. 4 illustrates a method 400 for performing a subretinal injection using injection apparatus 100 of FIG. 1A, according to certain embodiments. FIGS. 5A-5F illustrate each stage of method 400, according to certain embodiments. FIG. 4 and FIGS. 5A-5F are, therefore, described together herein for clarity.

At operation 402, injection apparatus 100 is loaded. In certain embodiments, injection apparatus 100 is loaded with a fluid and/or a drug. With injection apparatus 100 in the second state (shown in FIG. 3), drug container 144 may be loaded via suction through needle 116 or, alternatively, via injection through port 148. In some other embodiments, drug container 144 is pre-filled and subsequently inserted or clicked into injection apparatus 100. The drug is prevented from entering drug container bypass line 142 due to first outlet 158*a* of fluid selector 118 being closed off from fluid communication with drug container bypass line 142 in the second state.

Figure 5B:
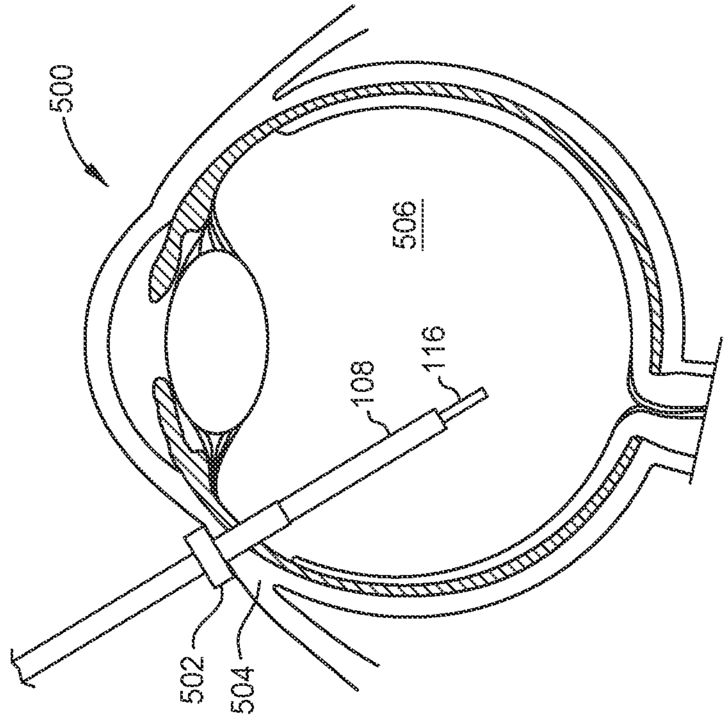
FIGS. 5A-5F illustrate each stage of the method of FIG. 4, according to certain embodiments.
Figure 5A:
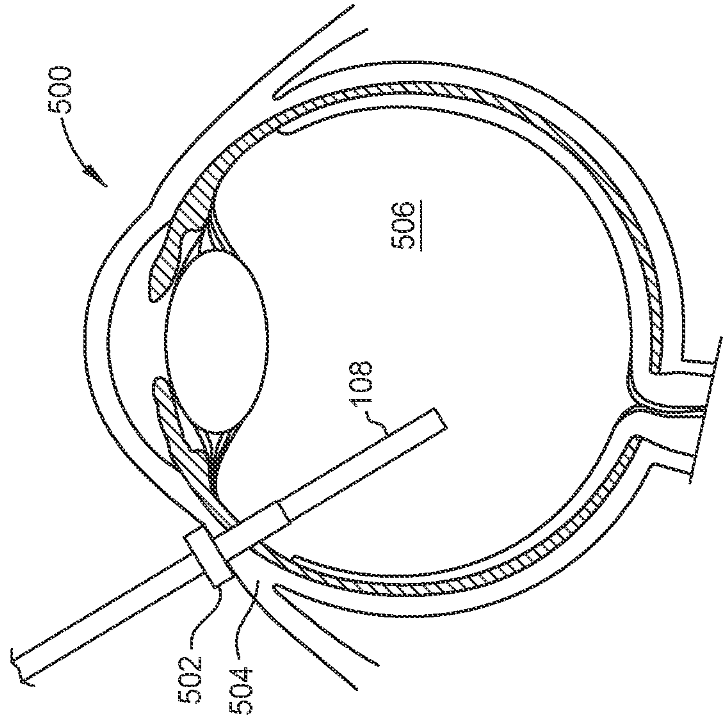

At operation 404, which is illustrated in FIG. 5A, outer tube 108 of injection apparatus 100 is inserted into eye 500. In the illustrated embodiments, outer tube 108 is inserted through a valved cannula 502, which is disposed through sclera 504, and further inserted into vitreous 506. At operation 406, which is illustrated in FIG. 5B, needle 116 is protracted from outer tube 108. Injection apparatus 100 is transitioned from the retracted state (shown in FIG. 2) to the protracted state (shown in FIG. 1B) by pushing or pulling actuator 110 in a distal direction in relation to housing 102. At operation 408, which is illustrated in FIG. 5C, needle 116 is inserted into subretinal space 508. Subretinal space 508 is located between retina 510 and RPE 512 of eye 500.

Figure 5D:
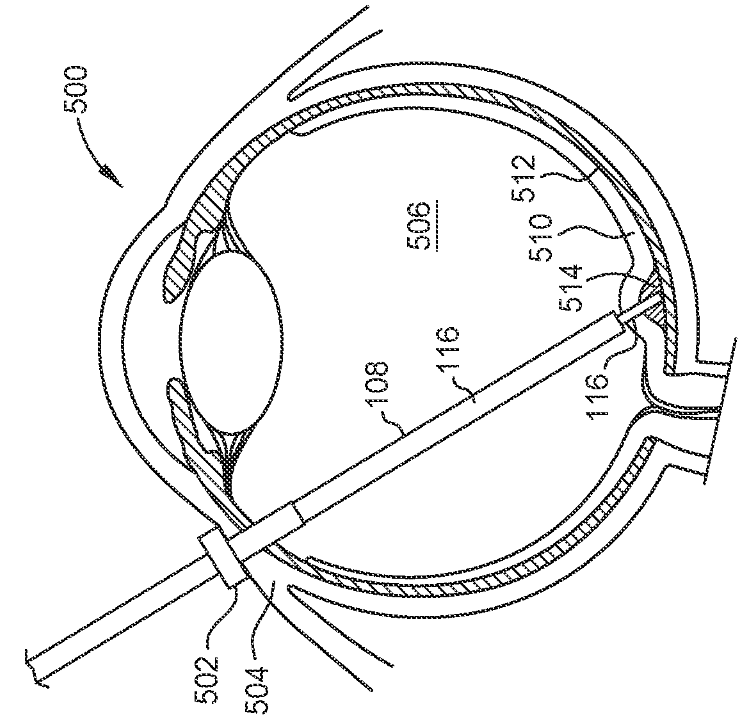
Figure 5C:
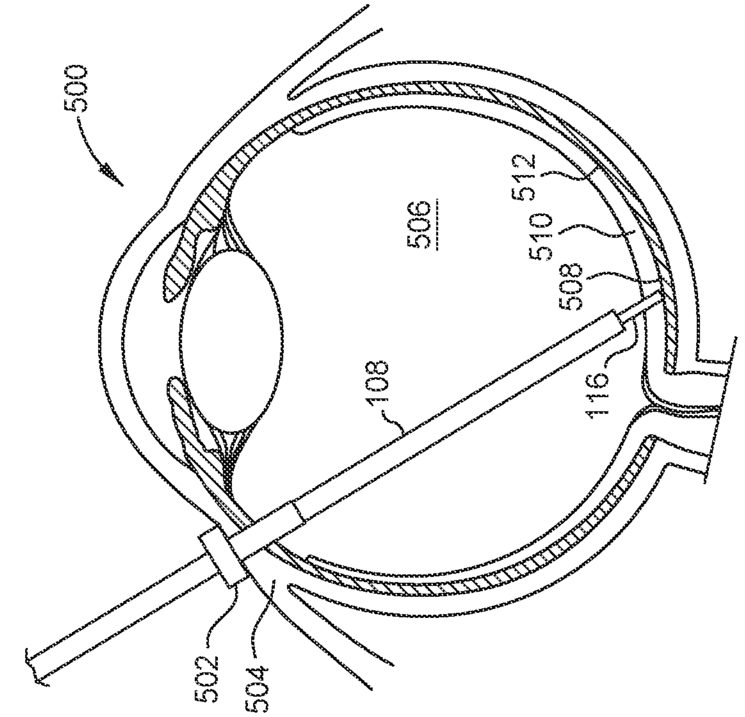

At operation 410, which is illustrated in FIG. 5D, fluid is injected into subretinal space 508 to create bleb 514. The fluid is injected from drug container bypass line 142 and/or syringe 120 with injection apparatus 100 in the first state (shown in FIG. 1D). Bleb 514 enlarges subretinal space 508 to ensure accurate drug injection. In certain embodiments, the fluid is BSS. At operation 412, drug is injected into subretinal space 508. The drug is injected from drug container 144 with injection apparatus 100 in the second state (shown in FIG. 3). In certain embodiments, to transition injection apparatus 100 from the first state to the second state, fluid selector 118 is moved to the second state by pushing cap 156*a*.

Figure 5F:
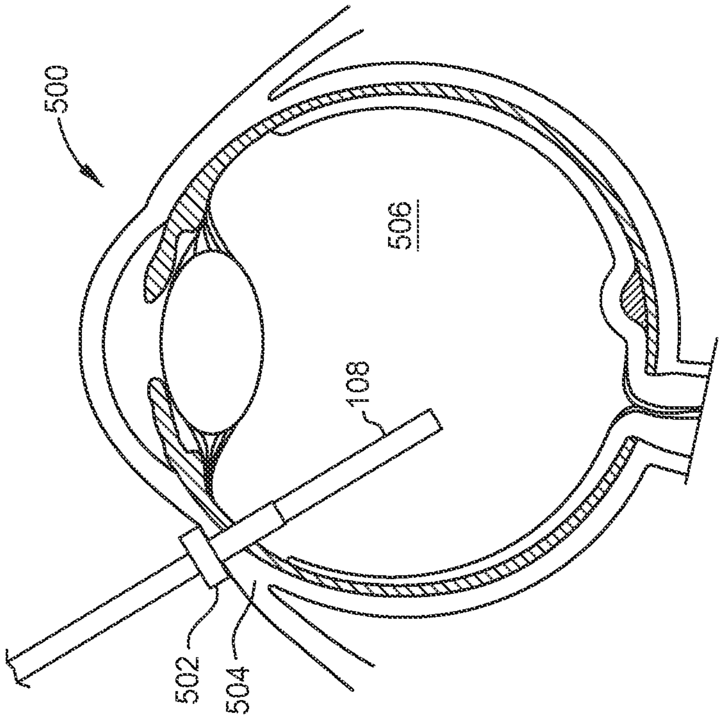
Figure 5E:
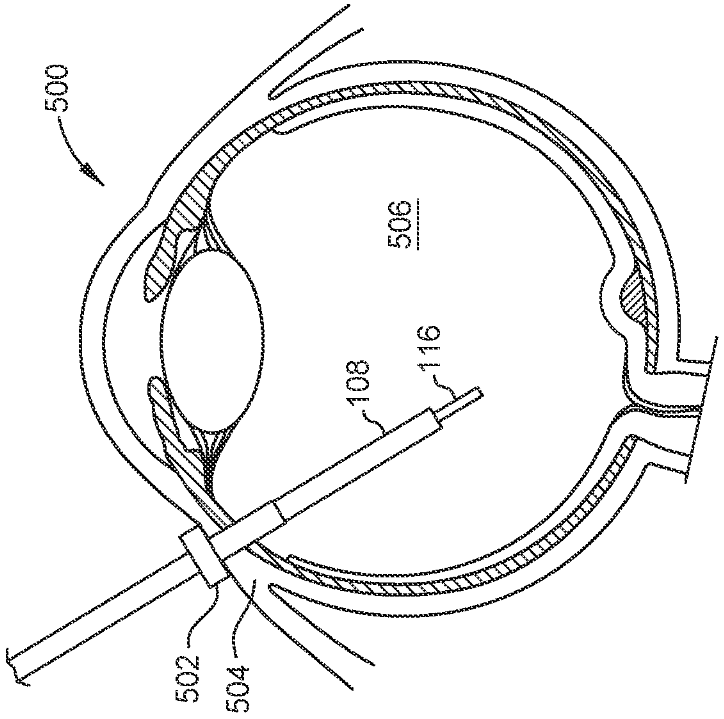

At operation 414, which is illustrated in FIG. 5E, needle 116 is removed from subretinal space 508. At operation 416, which is illustrated in FIG. 5F, needle 116 is retracted into outer tube 108. Injection apparatus 100 is transitioned from the protracted state (shown in FIG. 1B) to the retracted state (shown in FIG. 2) by pushing or pulling actuator 110 in a proximal direction in relation to housing 102. At operation 418, outer tube 108 is removed from eye 500.

Various alternative embodiments are described in detail below. Aspects of the following embodiments may be used in combination with injection apparatus 100 and/or method 400 described above.

Figure 6A:
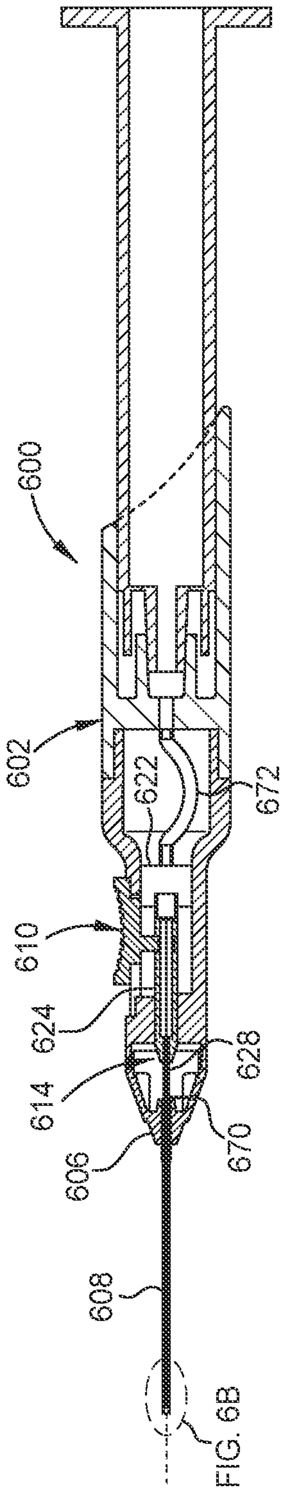
FIG. 6A is a cross-sectional view of another exemplary injection apparatus, according to certain embodiments.

FIG. 6A is a cross-sectional view of another exemplary injection apparatus 600, according to certain embodiments. Injection apparatus 600 may be used to perform method 400 as described in more detail below. FIG. 6A illustrates injection apparatus 600 in a retracted state. Injection apparatus 600 enables both a fluid and a drug to be administered from the same needle similar to other embodiments described herein. However, injection line sub-assembly 614 of injection apparatus 600 has two lumens for separately storing the fluid and the drug in contrast to drug container bypass line 142 and drug container 144 of injection apparatus 100 as described above. First piece 622 of sub-assembly is the same as injection apparatus 100, while second piece 624 of sub-assembly 614 and inner tube 628 each have two lumens. Independent control of loading and injection through the two different lumens of sub-assembly 614 is described in detail below with respect to FIGS. 9 and 10.

Figure 6B:
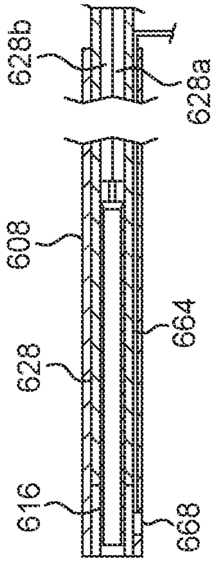
FIG. 6B is an enlarged cross-sectional view of a portion of FIG. 6A, according to certain embodiments.

FIG. 6B is an enlarged cross-sectional view of a portion of FIG. 6A, according to certain embodiments. As shown in FIG. 6B, a distal end of inner tube 628 is coupled to needle 616. Inner tube 628 has a first lumen 628*a* and a second lumen 628*b*. Injection apparatus 600 includes an aspiration line 664 for removing intravitreal fluid from the eye during injection of a fluid and/or drug into the subretinal space. Aspiration line 664 is disposed radially between outer tube 608 and inner tube 628. Aspiration line 664 extends from a first port 668 disposed through outer tube 608 to a second port 670 disposed through cap 606 of housing 602 (shown in FIG. 6A). First port 668 is located near a distal end of outer tube 608. When injection apparatus 600 is used to perform method 400, first port 668 remains in fluid communication with vitreous 506 when needle 616 is inserted into subretinal space 508 at operation 408 (see FIG. 5C). Aspiration line 664 may be connected to a surgical console for controlling aspiration rate/volume. Application of vacuum pressure through aspiration line 664 causes intravitreal fluid to pass through first port 668 from outside to inside outer tube 608. In certain embodiments, the surgical console is set to apply vacuum pressure so that the aspiration rate/volume matches the injection rate/volume of the fluid and/or drug being injected into the subretinal space in order to maintain intraocular pressure at equilibrium.

Figure 7B:
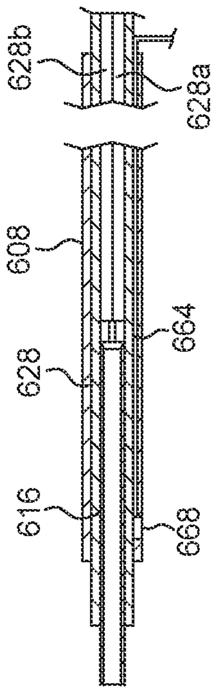
FIG. 7B is an enlarged cross-sectional view of a portion of FIG. 7A, according to certain embodiments.
Figure 7A:
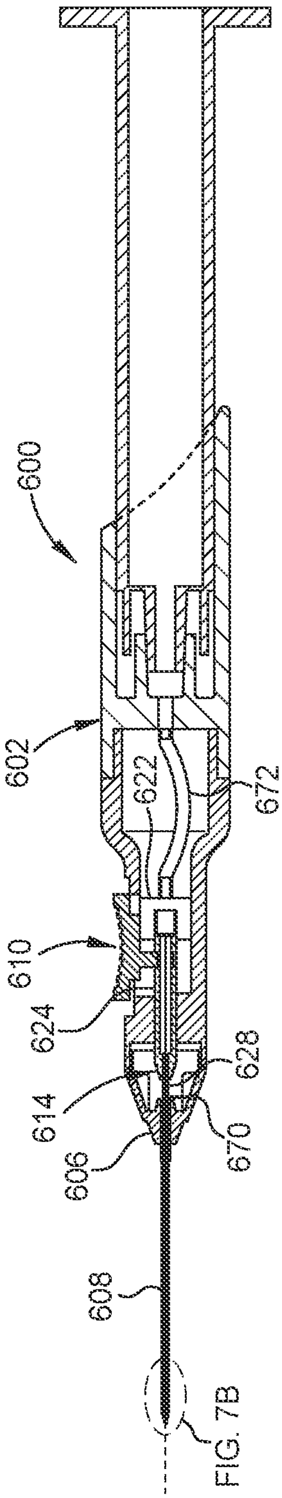
FIG. 7A illustrates the injection apparatus of FIG. 6A in a partially protracted state, according to certain embodiments.

FIG. 7A illustrates injection apparatus 600 in a partially protracted state, according to certain embodiments. In the partially protracted state, actuator 610 is moved only part way towards a distal end of housing 602. FIG. 7B is an enlarged cross-sectional view of a portion of FIG. 7A, according to certain embodiments. As shown in FIG. 7B, needle 616 is disposed at least partially outside a distal end of outer tube 608.

Figure 8A:
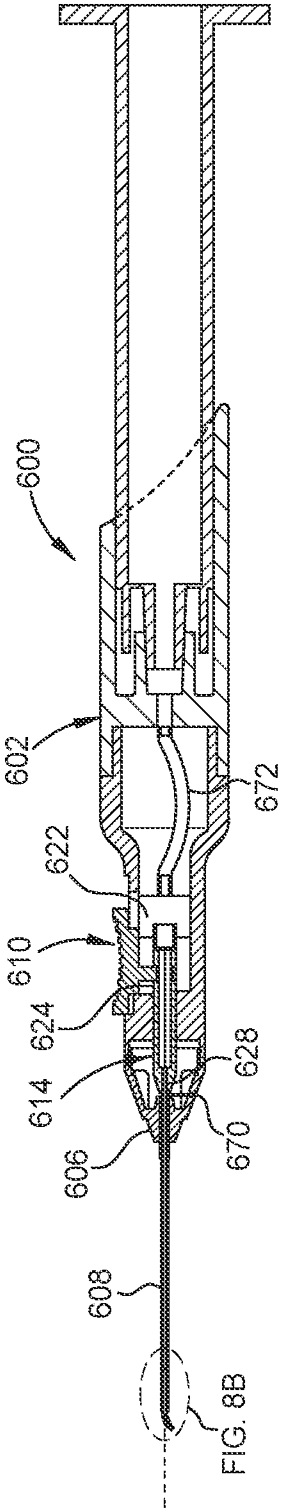
FIG. 8A illustrates the injection apparatus of FIG. 6A in a fully protracted state, according to certain embodiments.
Figure 8B:
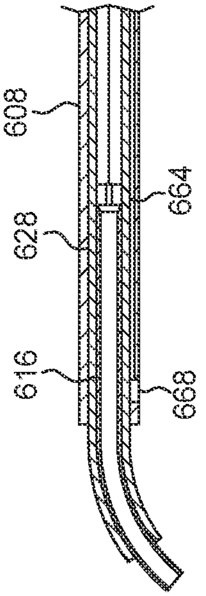
FIG. 8B is an enlarged cross-sectional view of a portion of FIG. 8A, according to certain embodiments.

FIG. 8A illustrates injection apparatus 600 in a fully protracted state, according to certain embodiments. In the fully protracted state, a distal end of actuator 610 contacts housing body 604 to prevent further movement of actuator 610 in the distal direction in relation to housing 602. FIG. 8B is an enlarged cross-sectional view of a portion of FIG. 8A, according to certain embodiments. As shown in FIG. 8B, needle 616 and inner tube 628 are curved in relation to outer tube 608. In some other embodiments, needle 616 is curved and inner tube 628 remains straight.

In certain embodiments, an angle of needle 616 is adjusted based on extension of needle 616 outside outer tube 608. In certain embodiments, the angle is within a range of about 0° to about 90° when measured relative to a longitudinal axis of outer tube 608. In use, the angle increases when transitioning from the partially protracted state (shown in FIG. 7B) to the fully protracted state (shown in FIG. 8B). When injection apparatus 600 is used to perform method 400, needle 616 is straight during insertion through retina 510 and into subretinal space 508 at operation 408 (see FIG. 5C) so that insertion of needle 616 is easier to control. After bleb 514 is at least partially formed at operation 410, needle 616 is further extended to a desired angle so that the curved part of needle 616 is aligned closer to parallel with RPE 512 compared to when the needle is straight (as shown in FIG. 5D), thereby reducing a potentially damaging jet of fluid directly on RPE 512 during subsequent injection.

Figure 9:
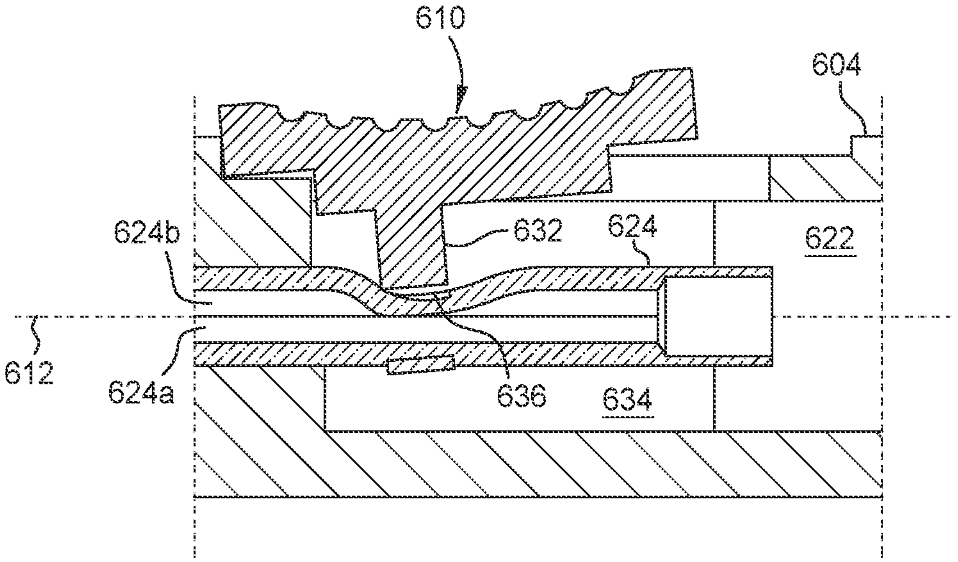
FIG. 9 illustrates the injection apparatus in a first state for injecting a fluid, according to certain embodiments.

FIG. 9 illustrates injection apparatus 600 in a first state for injecting a fluid, according to certain embodiments, which may be combined with other embodiments disclosed herein. FIG. 9 illustrates injection apparatus 600 in the fully protracted state (shown in FIG. 8A). Actuator 610 has a catch 632, which extends inside a cavity 634 of housing body 604. Catch 632 is located closer to a distal end of actuator 610 compared to catch 132 of injection apparatus 100. Catch 632 fits into a corresponding profile 636 formed in an outer surface of second piece 624. Profile 636 is in the shape of a circumferential recess formed in the outer surface of second piece 624. In the illustrated embodiments, a depth of the recess increases in a proximal direction, although other profiles are contemplated. In certain embodiments, catch 632 engages a distal end of second piece 624 at or near a location where second piece 624 is coupled to inner tube 628.

In the first state, injection apparatus 600 is configured to inject a fluid through a first lumen 624*a* of second piece 624 and through a corresponding lumen of inner tube 628. To transition injection apparatus 600 to the first state, actuator 610 is tilted in the distal direction in relation to housing 602. Actuator 610 rotates about an axis perpendicular to longitudinal axis 612 of housing body 604. In the first state, catch 632 compresses the outer surface of second piece 624 along one side, thereby blocking flow through second lumen 624*b*. The shape of profile 636 causes flow to be blocked through only second lumen 624*b* when actuator 610 is tilted in the distal direction. When fluid communication between second lumen 624*b* and needle 616 is closed, application of pressure through tubing 672 (shown in FIG. 6A) results in injection of the fluid from first lumen 624*a*. When injection apparatus 600 is used to perform method 400, the fluid may be loaded into first lumen 624*a* by applying suction through tubing 672 when injection apparatus 600 is in the first state.

Figure 10:
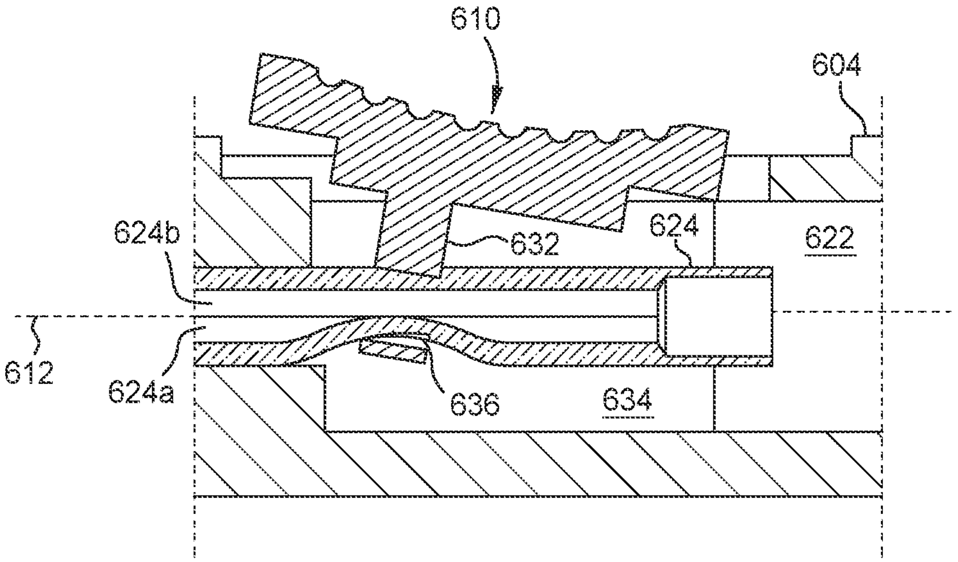
FIG. 10 illustrates the injection apparatus in a second state for injecting a drug, according to certain embodiments.

FIG. 10 illustrates injection apparatus 600 in a second state for injecting a drug, according to certain embodiments. FIG. 10 illustrates injection apparatus 600 in the fully protracted state (shown in FIG. 8A). In the second state, injection apparatus 600 is configured to inject a drug through second lumen 624*b* of second piece 624 and through a corresponding lumen of inner tube 628. To transition injection apparatus 600 to the second state, actuator 610 is tilted in a proximal direction in relation to housing 602, which is opposite of the first state. In the second state, catch 632 compresses an opposite side of the outer surface of second piece 624, thereby blocking flow through first lumen 624*a*. The shape of profile 636 causes flow to be blocked through only first lumen 624*a* when actuator 610 is tilted in the proximal direction. When fluid communication between first lumen 624*a* and needle 616 is closed, application of pressure through tubing 672 results in injection of the drug from second lumen 624*b*. When injection apparatus 600 is used to perform method 400, the drug may be loaded into second lumen 624*b* by applying suction through tubing 672 when injection apparatus 600 is in the second state.

In some other embodiments, independent injection of the fluid and/or drug through first lumen 624*a* and second lumen 624*b* is controlled by tilting actuator 610 side-to-side instead of front-to-back.

In summary, embodiments of the present disclosure improve the efficacy and safety of subretinal injection for treatment of ophthalmic conditions. In particular, embodiments of the present disclosure enable both a fluid and a drug to be administered from the same needle, which lessens potential for damage to the retina using typical practice described above which uses two separate injection steps with different needles.

While the foregoing is directed to embodiments of the present disclosure, other and further embodiments of the disclosure may be devised without departing from the basic scope thereof, and the scope thereof is determined by the claims that follow.

What is claimed is:

1. An apparatus for use in an ophthalmic subretinal injection, comprising:
- a housing coupled to a source of fluid;
- an injection line sub-assembly coupled to a distal end of the housing;
- a fluid selector coupled to the housing and movable between a first position and a second position;
- a drug container coupled to the housing and disposed between the fluid selector and the sub-assembly; and
- a drug container bypass line coupled to the housing and disposed between the fluid selector and the sub-assembly, wherein the drug container bypass line is connected in parallel with the drug container, wherein:
  - when the fluid selector is in the first position, a first outlet of the fluid selector is in fluid communication with the drug container bypass line for injecting the fluid through the drug container bypass line and into the sub-assembly and out of the distal end of the housing and into a subretinal space to form a bleb, and
  - when the fluid selector is in the second position, a second outlet of the fluid selector is in fluid communication with the drug container such that the apparatus is configured to drive, via the fluid, a drug out of the drug container for injecting the drug from the drug container into the sub-assembly and out of the distal end of the housing and into the subretinal space.

2. The apparatus of claim 1, further comprising an outer tube coupled to the distal end of the housing, wherein the sub-assembly is slidably disposed through the outer tube.

3. The apparatus of claim 2, wherein the sub-assembly comprises:
- a body disposed in the distal end of the housing;
- an inner tube coupled to a distal end of the body and at least partially disposed in the outer tube; and
- a needle coupled to a distal end of the inner tube.

4. The apparatus of claim 3, further comprising an actuator coupled to the body of the sub-assembly and slidable to retract and protract the sub-assembly, wherein:
- the needle is curved,
- when the sub-assembly is fully retracted, the needle is disposed entirely inside the outer tube, and
- when the sub-assembly is fully protracted, the needle is disposed at least partially outside a distal end of the outer tube.

5. The apparatus of claim 4, wherein the body of the sub-assembly comprises:
- a first inlet in fluid communication with the drug container;
- a second inlet in fluid communication with the drug container bypass line; and
- an outlet in fluid communication with the inner tube.

6. The apparatus of claim 5, wherein the drug container bypass line comprises a first piece of flexible tubing to allow relative movement between the sub-assembly and the housing during retraction and protraction of the sub-assembly, the apparatus further comprising:

a second piece of flexible tubing fluidly coupled between the drug container and the first inlet of the body, wherein the second piece of flexible tubing allows relative movement between the sub-assembly and the drug container during retraction and protraction of the sub-assembly.

7. The apparatus of claim 1, wherein:

the housing comprises a port at a proximal end thereof, wherein the port is configured to be coupled to a syringe, and the port is in fluid communication with an inlet of the fluid selector when the fluid selector is in either of the first or second positions.

8. The apparatus of claim 1, wherein the fluid selector comprises a pin disposed transverse to the housing, wherein:

the first and second outlets of the fluid selector are formed in the pin, and an inlet is formed in the pin in fluid communication with each of the first and second outlets.

9. The apparatus of claim 8, wherein:

each of the inlet and the first and second outlets are disposed transverse to a longitudinal axis of the pin, and the first and second outlets are spaced from each other relative to the longitudinal axis of the pin.

10. The apparatus of claim 8, wherein the fluid selector translates in a direction parallel to a longitudinal axis of the pin to move between the first and second positions.

* * * * *